United States Patent [19]

Zengel et al.

[11] Patent Number: 4,558,135
[45] Date of Patent: Dec. 10, 1985

[54] PROCESS FOR THE PREPARATION OF DITHIAZOLYL DISULFIDES

[75] Inventors: Hans-Georg Zengel, Kleinwallstadt; Manfred Bergfeld, Erlenbach/Mechenhard; Ludwig Eisenhuth, Elsenfeld, all of Fed. Rep. of Germany

[73] Assignee: Akzona Incorporated, Asheville, N.C.

[21] Appl. No.: 324,181

[22] Filed: Nov. 23, 1981

[30] Foreign Application Priority Data

Apr. 2, 1981 [DE] Fed. Rep. of Germany ....... 3113298

[51] Int. Cl.$^4$ ............................................. C07D 277/70
[52] U.S. Cl. .................................... 548/158; 548/182; 548/183; 548/184
[58] Field of Search ............... 548/166, 158, 182, 183, 548/184; 568/28

[56] References Cited

U.S. PATENT DOCUMENTS

| 2,031,714 | 2/1936 | Kallner et al. | 548/158 |
| 3,086,018 | 4/1963 | Hardman | 548/166 |
| 3,143,574 | 8/1964 | Brown | 568/26 |
| 3,654,297 | 4/1972 | Goulandris | 548/158 |
| 3,925,401 | 12/1975 | Janin | 548/158 |
| 4,307,236 | 12/1981 | Zengel et al. | 548/158 |

FOREIGN PATENT DOCUMENTS 1407649 9/1975 United Kingdom .

OTHER PUBLICATIONS

Georg Thieme Verlag Stuttgart 1978, p. 23 entitled, "Reaktionen der Organischen Synthese" by Cesare Ferri.
Chemische Berichte, vol. 93, 1960, pp. 428–434 entitled, "Roland Mayer and Peter Barthel".
Chemistry and Industry, 1963, pp. 734 and 735, "Thiol Anion Oxidations Catalysed by Transition Metal Pyrophosphates", by T. J. Wallace, A. Schriesheim and H. B. Jonassen.
Chemical Abstracts, vol. 60, 1964, columns 2843 and 2844 entitled, "Aliphatic and Aryl Disulfides and Polysulifides".

Primary Examiner—Robert T. Bond
Assistant Examiner—D. B. Springer
Attorney, Agent, or Firm—Parkhurst & Oliff

[57] ABSTRACT

A process for the preparation of dithiazolyl disulfides by the catalytic oxidation of a 2-mercaptothiazole with ammonia and either oxygen or an oxygen-containing gas at a temperature of between 0° and 150° C.

8 Claims, No Drawings

PROCESS FOR THE PREPARATION OF DITHIAZOLYL DISULFIDES

BACKGROUND OF THE INVENTION

Process for the preparation of dithiazolyl disulfides are known in the art, and include the processes described in German Patent No. 23 55 897 and pending U.S. Pat. No. 3,654,297 German patent application No. P 29 44 225.9-44, which is also pending U.S. patent application Ser. No. 196,897, filed Oct. 14, 1980, now U.S. Pat. No. 4,307,236. These processes comprise the catalytic oxidation of 2-mercaptobenzothiazole with oxygen or an oxygen-containing gas in the presence of a solvent and at a temperature between 0° and 150° C. The disadvantages of the two prior processes (U.S. Pat. No. 3,654,297 and DE-OS No. 23 55 897) were already discussed extensively in DE-OS No. 29 44 225. In the case of U.S. Pat. No. 3,654,297 cobaltphthalocyanine sulfates are used, which are comparatively expensive while production and industrial use are problematical. In the case of DE-OS No. 23 55 897 iron chloride, especially ferric chloride is used as catalyst in comparatively large amounts (from 0.8 to 1.5 mole per mole 2-mercaptobenzothiazole). The decisive disadvantage of this process is however that the iron precipitates in form of basic salts during the reaction and that the resulting dibenzothiazolyldisulfide is considerably contaminated by iron and cannot be used without complicated purification. According to the process of DE-OS No. 29 44 225 the catalytic oxidation of mercaptobenzothiazoles with oxygen or an oxygen-containing gas is carried out in the presence of a solvent and at temperatures between 0° and 150° C., whereby the catalyst is a tertiary amine or optionally a heavy metal or heavy metal compound. Despite high yields of dithiazolyldisulfides this process is disadvantageous in that it requires realitively expensive catalysts in large amounts (tert. amines). Moreover losses in tert. amines must be expected from oxidative degradation, and during recovery of the reaction product.

SUMMARY OF THE INVENTION

The invention discloses a process for the preparation of dithiazolyl-(2,2')-disulfides, which are useful rubber vulcanizing agents, of the general formula

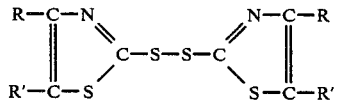

wherein R and R' may be the same, or different, and may represent a hydrogen atom, a halogen atom, a nitro group, a hydroxyl group, or mono- or multi-substituted organic radical, such as an alkyl or alkoxy radical with 1 to 6 carbon atoms, or a cycloalkyl or aryl radical with 6 to 12 carbon atoms, wherein the substituents may be a halogen atom, a nitro group, a hydroxyl group, or an alkyl or alkoxy radical with 1 to 5 carbon atoms, or in which R and R' jointly form the radical

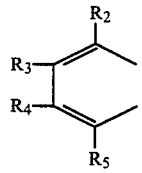

wherein $R_2$, $R_3$, $R_4$ and $R_5$ may be the same, or different and may have the same meaning as R and R', by means of the catalytic oxidation of a 2-mercaptothiazole of the general formula

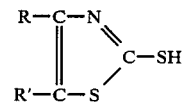

in which R and R' have the meaning indicated above, by means of oxygen, or a gas containing oxygen, in the presence of a solvent and ammonia at temperatures in the range from 0° to 150° C., and further optionally utilizing a heavy metal or heavy metal compound as catalyst. The substituted 2-mercaptothiazoles and their preparation are known, for example, they can be made by the procedure disclosed in the aforesaid U.S. Pat. No. 4,307,236.

The suprising aspect of the present invention is that the catalytic oxidation of 2-mercaptothiazoles to dithiazolyl(2,2')-disulfides is effected not merely by a tertiary amine, or by a tertiary amine and a heavy metal or heavy metal compound, but also by ammonia or ammonia and a heavy metal or heavy metal compound.

Surprisingly, by using ammonia the by-products expected according to literature (e. g. sulfenamides; see DE-OS No. 23 49 934, pages 5 and 16) were not observed.

The catalytic oxidation of 2-mercaptothiazoles to dithiazolyl-(2,2')-disulfides may be effected by ammonia alone. By adding a heavy metal catalyst, the reaction rate is increased considerably. The quantity of ammonia can be varied within a wide range; however, preference is given to ammonia in quantities from 0.1% to 6% by weight, referred to the reaction mixture. The reaction mixture comprises the 2-mercaptothiazoles and the solvent.

The substituents R to $R_5$ are preferably chlorine or bromine radicals, a hydroxyl group, a nitro group, a straight-chain or branched-chain alkyl radical with 1 to 4 carbon atoms, such as methyl, ethyl, propyl, isopropyl, butyl, or tertiary butyl radicals, an alkoxy radical with 1 to 4 carbon atoms, such as methoxy, ethoxy, propoxy, or butoxy, or a phenyl, tolyl, ethylphenyl, nitrophenyl, chlorophenyl, bromophenyl, or naphthyl radical.

DESCRIPTION OF THE PREFERRED EMBODIMENTS

The process pursuant to the invention is especially useful in the preparation of dibenzothiazolyl-(2,2')-disulfide, the most important representative of this class of compounds. It can, however, be used successfully for the preparation of additional compounds of this type. For the preferred preparation of dibenzothiazolyl-(2,2')disulfide, 2-mercaptobenzothiazole is used as an initial material. Other mercaptothiazoles suitable as initial materials for the preparation of dithiazolyl-(2,2')-disulfides of the general formula as set forth hereinabove include the compounds mentioned in German published patent application disclosure No. 23 55 897, such as
2-mercaptothiazole
2-mercapto-4-methylthiazole
2-mercapto-4-ethylthiazole
2-mercapto-4-n-propylthiazole
2-mercapto-4-n-butylthiazole
2-mercapto-4,5-dimethylthiazole
2-mercapto-4,5-di-n-butylthiazole
2-mercapto-4-phenylthiazole
2-mercapto-5-chloro-4-phenylthiazole
2-mercapto-4-p-bromophenylthiazole
2-mercapto-4-m-nitrophenylthiazole
2-mercapto-4-m-chlorophenylthiazole
2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole
2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole
2-mercapto-5-chloro-6-methoxybenzothiazole
2-mercapto-5-chloro-4-nitrobenzothiazole
2-mercapto-5-chloro-6-nitrobenzothiazole
2-mercapto-4,5-dichlorobenzothiazole
2-mercapto-4,7-dichlorobenzothiazole
2-mercapto-5-nitrobenzothiazole
2-mercapto-6-nitrobenzothiazole
2-mercapto-4-phenylbenzothiazole
2-mercapto-naphthothiazole
2-mercapto-6-hydroxybenzothiazole.

As previously stated, the ammonia catalyst may be used alone or jointly with a heavy metal or a heavy metal compound. Suitable metal cocatalysts include iron, cobalt, nickel, copper, chromium, zinc, manganese, silver, vanadium, molybdenum, cerium and their oxides. Other suitable cocatalysts include the inorganic or organic salts or complex compounds of these metals. Copper and its several compounds are preferred heavy metal cocatalysts.

The heavy metal or heavy metal compound is used in quantities of less than 0.1% by weight, referred to the 2-mercaptothiazole. Since traces of a copper cocatalyst display considerable catalytic activity and lead to good dithiazyl disulfide yields, it is thus possible, to use small catalyst quantities and to circulate the mother liquor repeatedly without having to accept a decline in reaction rate.

The copper compounds that may be considered as suitable catalysts include all mono- or divalent inorganic, simple organic, or complex copper salts. Examples of suitable monovalent copper salts include copper (I) chloride, bromide and iodide; addition compounds of these copper (I) halides with carbon monoxide; complex copper (I) salts such as the alkali chlorocuprates; complex ammoniates of copper (I) cyanide, e. g. cyanocuprates such as potassium tricyanocuprate (I); double salts with copper (I) rhodanide; copper (I) acetate, copper (I) sulfite; complex double sulfides of copper (I) acetate and copper (I) sulfite; and complex double sulfides of copper (I) sulfide and alkali poly-sulfides. Examples of suitable copper (II) salts are copper (II) chloride, bromide, sulfide, sulfate, nitrate, nitrite, rhodanide, and cyanide; and copper (II) salts of carboxylic acids, such as copper (II) acetate, as well as the complex ammoniates of copper (II) salts. Metallic copper and copper (I) oxide are also very well suited as cocatalysts. Preferable cocatalysts include copper powder, copper (I) chloride, copper (II) acetate, copper (II) sulfate, copper (II) oleate, copper (II) acetylacetonate, copper (II) sulfide, or copper (I) oxide.

Since the heavy metal compound is used in small quantities, not only easily soluble heavy metal compounds are suitable, but also those heavy metal compounds which exhibit only very little solubility, or of which only traces are soluble in the solvent. As solvents one can use all oxidation-resistant, organic solvents. Examples thereof are alcohols, dimethyl formamide, benzene, toluene and chlorobenzene. Suitable alcohols include those aliphatic alcohols with 1 to 10 carbon atoms, as for example, methanol, ethanol, propanol, isopropanol, secondary butanol, tertiary butanol, pentanol, isopentanol, tertiary pentanol, hexanol, heptanol and octanol. Preferable solvents include toluene and isopropanol. The concentration of the solvent is not critical. In general, the quantity of solvent is within a range from 200% to 1200% by weight, referred to the 2-mercaptothiazole used. Larger quantities of solvent should be avoided for reasons of economy, as more solvent necessitates more ammonia. Oxygen or a gas containing oxygen, preferably air, is used as an oxidizing agent. Conversion rate and selectivity increase with increasing oxygen pressure, or partial pressure. In general, this partial pressure is between 0.1 to 150 bar. For reasons of economy, the preferable range of oxygen pressures, or partial pressures, is from 2 to 10 bar. The reaction temperature is from 0° to 150° C., preferably from 20° to 90° C., and in particular from 60° to 80° C. As lower temperatures, the reaction rate declines; at higher temperature, the selectivity of the reaction is reduced.

As a rule, the duration of the reaction is 0.5 to 6.5 hours. Under the mentioned preferred pressure and temperature conditions, and in the presence of a copper cocatalyst, the reaction duration is less than an hour with an 80% conversion rate.

The process of the invention can be carried out in a simple manner by passing the oxygen or the oxygen-containing gas into or through the solution consisting of the 2-mercaptothiazole, solvent, heavy metal catalyst and ammonia, under the indicated pressure and temperature conditions. Since any unreacted 2-mercaptothiazole remains dissolved in the solvent, processing of the reaction mixture is very simple. The precipitated reaction product is either filtered or centrifuged off and the mother liquor is mixed with fresh 2-mercaptothiazole and circulated. Depending upon the initial level of the heavy metal catalyst concentration, fresh catalyst must be added after a certain number of reaction cycles. In addition, the water of reaction formed during the conversion should preferably be removed from the mother liquor when its content has risen to more than 10% by weight, referred to the mother liquor. Nearly quantitative yields and selectivities of more than 99% are obtained with the process pursuant to the invention. The resulting dithiazolyl-(2,2')-disulfides exhibit high purity and can be used as rubber vulcanizing agents without any further purification. In contrast to the two know processes using a tertiary amine, in which a 2-mercaptobenzothiazole is likewise oxidized by means of oxygen, the process pursuant to the invention is advantageous in that simple and cheap catalysts are used in very small quantities and that these catalysts can be circulated with the mother liquor without any noticeable decline in their activity.

The following preferred embodiments illustrate the invention in detail:

EXAMPLE 1

40 g (0.24 mol) of 2-mercaptobenzothiazole (MBT), 4 mg (0.02×10⁻³ mol) of copper (II) acetate, (Cu(OAc)$_2$. H$_2$O), 4.08 g (0.24 mol) of ammonia, and 120 g of isopropanol are placed in a glass autoclave equipped with a jacket for the circulation of a heating liquid, a thermometer, a pressure measuring device and a stirring device. The reaction mixture is heated to 70° C., stirred vigorously, and placed under an oxygen pressure of 4 bar. Absorption of oxygen is noted immediately and a precipitate, dibenzothiazyl disulfide (MBTS), is formed. After 6.5 hours the reaction is discontinued and the precipitate is filtered off, washed with isopropanol, and dried under a vacuum at 50° C. 37.8 g of a product are obtained in this manner. Upon elementary analysis, IR, NMR and MS, the product formed is found to correspond to dibenzothiazyl disulfide. The purity is found to be 100% upon chromatographic analysis (melting point 178° C.).

Another 0.5 g of dibenzothiazyl disulfide is isolated from the mother liquor by means of extractive separation with methanol. The quantity of unreacted 2-mercaptobenzothiazole in the residue is determined by potentiometric titration with aqueous silver nitrate solution to be 0.9 gram. Thus, the yield of dibenzothiazyl disulfide amounts to 96.4% of theoretical, at a mercaptobenzothiazole conversion rate of 97.8%.

EXAMPLE 2

The work is carried out as in Example 1, but without the addition of copper (II) acetate. In this case, the mercaptobenzothiazole conversion after 6.5 hours is 89.9% and the yield of dibenzothiazyl disulfide is 34.9 g, corresponding to 87.9% of theoretical.

EXAMPLE 3

A solution of 40 g (0.24 mol) of 2-mercaptobenzothiazole, 22.4 mg (0.1×10⁻³ mol) of Mn(OAc)$_2$. 4H$_2$O and 4.08 g (0.24 mol) of ammonia in 120 g of methanol is in the manner and reaction equipment described in Example 1 reacted with oxygen at an oxygen pressure of 4 bar and a reaction temperature of 55° C. After a reaction time of 3 hours, one obtains dibenzo thiazyl disulfide at a yield of 35.9 g, corresponding to 90.3% of theoretical. The conversion rate is determined to be 92.1%.

EXAMPLES 4 to 7

The quantity of ammonia is varied in the following examples. The work is carried out in the manner described in Example 1 (4 mg (0.02 mmol) of Cu(OAc)$_2$. H$_2$O, reaction temperature 70° C.). The oxygen pressures used, the reaction times, as well as the conversion rates and yields obtained in this manner are compiled in the following table.

| Example No. | MBT mmol | NH$_3$ mmol | O$_2$-press bar | reaction time, hrs. | MBT-conver. % | MBTS yield % of theory |
|---|---|---|---|---|---|---|
| 4 | 240 | 480 | 4 | 6.5 | 97.5 | 94.0 |
| 5 | 240 | 150 | 4 | 6.0 | 92.7 | 91.8 |
| 6 | 240 | 50 | 5 | 6.5 | 94.3 | 93.0 |
| 7 | 240 | 10 | 4 | 5.0 | 58.1 | 57.2 |

EXAMPLE 8

A solution of 40 g (0.24 mol) of 2-mercaptobenzothiazole, 4 mg (0.02 mmol) of Cu(OAc)$_2$. H$_2$O, and 4.08 g (0.24 mol) of ammonia in 120 g of methanol is reacted with oxygen in the manner and reaction equipment described in Example 1. The oxygen pressure is 4 bar and the reaction temperature 55° C. After 6 hours of reaction, the conversion rate is 96.5% and the yield of dibenzothiazyl disulfide is 38.2 g, corresponding to 96.1% of theoretical.

EXAMPLE 9

A solution of 40 g (0.24 mol) of 2-mercaptobenzothiazole, 4 mg (0.02 mmol) of Cu(OAc)$_2$. H$_2$O and 4.08 g (0.24 mol) of ammonia in 120 g of ethanol is reacted with oxygen in the manner and reaction equipment described in Example 1. The oxygen pressure is 5 bar and the reaction temperature 65° C. After 6 hours of reaction, the conversion rate is 98.2% and the yield of dibenzothiazyl disulfide is 38.3 g, corresponding to 96.4% of the theoretical.

EXAMPLES 10 to 14

In the following examples, other heavy metal catalysts are used. 40 g (0.24 mol) of 2-mercaptobenzothiazole in 120 g of isopropanol are oxidized in the presence of 4.08 g of ammonia (0.24 mol) at 70° C. and an oxygen pressure of 4 bar and in the manner as set forth in Example 1. The results obtained when using different metal catalysts are compiled in the following table. The anion (acac) is acetylacetonate, (C$_5$H$_7$O$_2$).

| Metal catalyst (10⁻⁴ mol) | reaction time, min | MBT conversion % | MBTS yield % of theoretical |
|---|---|---|---|
| Fe(acac)$_3$ | 80 | 94.3 | 93.5 |
| Co(NO$_3$)$_2$ | 135 | 92.5 | 91.7 |
| VO(acac)$_2$ | 240 | 86.3 | 84.4 |
| Ce(NO$_3$)$_3$ | 200 | 75.2 | 73.6 |
| MoO$_2$(acac)$_2$ | 280 | 79.7 | 77.3 |

What we claim is:

1. In a process for the preparation of dithiazolyl-(2,2')-disulfides of the formula

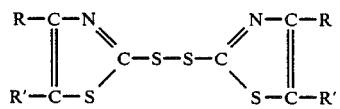

wherein R and R' may be the same or different, and represent a hydrogen atom, a halogen atom, a nitro group, a hydroxyl group, an alkyl or alkoxy radical with 1 to 6 carbon atoms, a cycloalkyl or aryl radical with 6 to 12 carbon atoms, wherein said alkyl, alkoxy, cycloalkyl or aryl radical are substituted with at least one substituent selected from the group consisting of a halogen atom, a nitro group, a hydroxyl group, and an alkyl or alkoxy radical with 1 to 5 carbon atoms; or R an R' jointly may form the radical

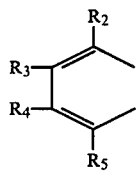

whereby $R_2$, $R_3$, $R_4$, and $R_5$ may be the same or different and have the same meaning as R and R', by means of the catalytic oxidation of a 2-mercaptothiazole of the formula

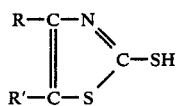

in which R and R' are as set forth above, by means of oxygen or an oxygen containing gas, the improvement consisting essentially of reacting said 2-mercaptothiazole in the presence of a catalytic amount of ammonia and a solvent at temperatures in the range from 0° to 150° C.

2. The process as set forth in claim 1, further utilizing ammonia in quantities from 0.1 to 6% by weight, referred to said 2-mercaptothiazole and solvent.

3. The process as set forth in claim 1, further utilizing a heavy metal or heavy metal compound as a catalyst, in quantities of less than 0.1% by weight, referred to the 2-mercaptobenzothiazole.

4. The process as set forth in claim 2, further utilizing a heavy metal or heavy metal compound as a catalyst, in quantities of less than 0.1% by weight, referred to the 2-mercaptobenzothiazole.

5. The process as set forth in claim 3, wherein said heavy metal or heavy metal compound is metallic copper or a copper compound.

6. The process as set forth in claim 4, wherein said heavy metal or heavy metal compound is metallic copper or a copper compound.

7. The process as set forth in claim 5, wherein said heavy metal or heavy metal compound comprises copper powder, copper (I) chloride, copper (II) acetate, copper (II) sulfate, copper (II) oleate, copper (II) acetylacetonate, copper (II) sulfide, or copper (I) oxide.

8. The process as set forth in claim 6, wherein said heavy metal or heavy metal compound comprises copper powder, copper (I) chloride, copper (II) acetate, copper (II) sulfate, copper (II) oleate, copper (II) acetylacetonate, copper (II) sulfide, or copper (I) oxide.

* * * * *

UNITED STATES PATENT AND TRADEMARK OFFICE
CERTIFICATE OF CORRECTION

PATENT NO. : 4,558,135

DATED : December 10, 1985

INVENTOR(S) : Hans-Georg ZENGEL et al

It is certified that error appears in the above-identified patent and that said Letters Patent is hereby corrected as shown below:

Column 2, line 37, change "sulfenamides;" to --sulfonamides;--.

Signed and Sealed this

Eighteenth Day of March 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.  : 4,558,135

DATED       : December 10, 1985

INVENTOR(S) : Hans-Georg ZENGEL et al

It is certified that error appears in the above-identified patent and that said Letters Patent is hereby corrected as shown below:

Column 1, line 10, after "3,654,297" insert --and--.

Column 2, line 37, change "sulfonamides;" to --sulfenamides;--.

Column 5, line 3, change "know" to --known--.

Signed and Sealed this

Eighth Day of July 1986

[SEAL]

Attest:

DONALD J. QUIGG

Attesting Officer

Commissioner of Patents and Trademarks